United States Patent
Zhang (10) Patent No.: US 10,530,992 B2
(45) Date of Patent: Jan. 7, 2020

(54) DETECTION METHOD, DETECTION SYSTEM, AND DETECTION DEVICE FOR FLEXIBLE SUBSTRATE

(71) Applicant: Wuhan China Star Optoelectronics Technology Co., Ltd., Wuhan, Hubei (CN)

(72) Inventor: Chun Zhang, Guangdong (CN)

(73) Assignee: Wuhan China Star Optoelectronics Technology Co., Ltd, Wuhan, Hubei (CN)

( * ) Notice: Subject to any disclaimer, the term of this patent is extended or adjusted under 35 U.S.C. 154(b) by 440 days.

(21) Appl. No.: 15/326,679

(22) PCT Filed: Jan. 16, 2017

(86) PCT No.: PCT/CN2017/071223
§ 371 (c)(1),
(2) Date: Jan. 17, 2017

(87) PCT Pub. No.: WO2018/120312
PCT Pub. Date: Jul. 5, 2018

(65) Prior Publication Data
US 2018/0343384 A1 Nov. 29, 2018

(30) Foreign Application Priority Data
Dec. 28, 2016 (CN) .......................... 2016 1 1236724

(51) Int. Cl.
*H04N 5/232* (2006.01)
*G06T 7/20* (2017.01)
(Continued)

(52) U.S. Cl.
CPC ......... *H04N 5/23218* (2018.08); *G01N 21/95* (2013.01); *G06T 7/0004* (2013.01);
(Continued)

(58) Field of Classification Search
CPC ............... H04N 5/23218; G01N 21/95; G01N 2021/9513; G06T 7/0004; G06T 7/20; G06T 2207/30121
See application file for complete search history.

(56) References Cited

U.S. PATENT DOCUMENTS

2002/0035435 A1\* 3/2002 Ninomiya .......... G01N 21/9501
702/35
2007/0237385 A1\* 10/2007 Kato .................. G01N 21/9501
382/149
(Continued)

FOREIGN PATENT DOCUMENTS

CN 102778460 A 11/2012
CN 203259481 U 10/2013
(Continued)

*Primary Examiner* — Jamil Ahmed
(74) *Attorney, Agent, or Firm* — Andrew C. Cheng (57) ABSTRACT

The present invention provides a detection method, a detection system, and a detection device for flexible substrate; and the detection method comprises: obtaining the light intensity distribution by parallel light with the same intensity transmitted through the flexible substrate; finding a difference point of light intensity from the light intensity distribution; obtaining a position of the difference point of light intensity corresponding to the flexible substrate, and the position is treated as an abnormal position in the flexible substrate. Wherein the difference point of light intensity is a point where the light intensity is different from the light intensity of the surrounding area. The abnormal positions can be obtained by the detection method of the present invention.

14 Claims, 5 Drawing Sheets

(51) Int. Cl.
*G01N 21/95* (2006.01)
*G06T 7/00* (2017.01)

(52) U.S. Cl.
CPC ........ *G06T 7/20* (2013.01); *G01N 2021/9513* (2013.01); *G06T 2207/30121* (2013.01)

(56) References Cited

U.S. PATENT DOCUMENTS

| | | |
|---|---|---|
| 2013/0248692 A1 | 9/2013 | Cheng |
| 2013/0278925 A1 | 10/2013 | Cheng |
| 2016/0332182 A1 | 11/2016 | Yin |
| 2017/0115230 A1 | 4/2017 | Kurihara et al. |

FOREIGN PATENT DOCUMENTS

| | | | | |
|---|---|---|---|---|
| CN | 203396719 U | * | 1/2014 | ........... G01N 21/958 |
| CN | 203396719 U | | 1/2014 | |
| CN | 104458767 A | | 3/2015 | |
| CN | 204287068 U | | 4/2015 | |
| CN | 104634262 A | | 5/2015 | |
| JP | 2006071521 A | | 3/2006 | |
| WO | WO2016121628 A1 | | 8/2016 | |

\* cited by examiner

DETECTION METHOD, DETECTION SYSTEM, AND DETECTION DEVICE FOR FLEXIBLE SUBSTRATE

FIELD OF THE INVENTION

The present invention relates to a technology of liquid crystal display, and more particularly, to a detection method, a detection system, and a detection device for flexible substrate.

DESCRIPTION OF PRIOR ART

With the development of display technology, flexible display technology has gradually become a hot research field of flat panel display, organic light-emitting diode (OLED) display has gradually become the general direction of the development of the display. The manufacture of flexible substrate is a pre-process of the OLED display, directly correlating and influencing the quality of the subsequent manufacture of OLED display.

The flexible substrate is mainly made from flexible films by coating flexible organic materials. Common organic materials include liquid polyimide amide acid (PAA,) polyethylene terephthalate (PET,) polyethylene naphthalate (PEN,) etc. Because of the organic material properties (particularly high viscosity, typically 3000-10000 cP,) it is easy to occur an abnormality such as air bubbles in the manufacturing process of the flexible substrate. If the flexible substrates with abnormalities enter the subsequent process of display, will result in the final preparation of the products appear poor display problems, and wasting manpower and material resources in the manufacturing process.

SUMMARY OF THE INVENTION

In view of this, the present invention provides a detection system, and a detection device for flexible substrate. The detection method of flexible substrate of the present invention can obtain a position where an abnormality occurs in the flexible substrate.

In order to solve the above-mentioned technical problems, the present invention provides a technical solution: providing a detection system for flexible substrate, which comprises: a light intensity distribution acquisition module for obtaining the light intensity distribution by parallel light with the same intensity transmitted through the flexible substrate; an analysis module for finding a difference point of light intensity from the light intensity distribution; and a position acquisition module for obtaining a position of the difference point of light intensity corresponding to the flexible substrate, and the position is treated as an abnormal position in the flexible substrate.

Wherein the difference point of light intensity is a point where the light intensity is different from the light intensity of the surrounding area.

Wherein the position acquisition module comprises: a first coordinate acquiring unit for obtaining a first coordinate of the difference point of light intensity in a currently used coordinate system; and a second coordinate acquiring unit for converting the first coordinate into a coordinate system of the flexible substrate to obtain a second coordinate treated as an abnormal position where an abnormality exists in the flexible substrate.

Wherein the detection system further comprises: an instruction sending module for sending a photographing instruction to a photographing device including information of the abnormal position to cause the photographing device to take an image of the abnormal position in the flexible substrate.

Wherein the detection system further comprises: a first information feedback module for feeding back the information of the abnormal position to the display interface.

Wherein the detection system further comprises: a second information feedback module for counting the number of the difference points of light intensity and feeding back the number of the difference points of light intensity to the display interface.

The present invention further provides a technical solution: providing a detection method for flexible substrate, which comprises: obtaining the light intensity distribution by parallel light with the same intensity transmitted through the flexible substrate; finding a difference point of light intensity from the light intensity distribution; and obtaining a position of the difference point of light intensity corresponding to the flexible substrate and taking the position treated as an abnormal position in the flexible substrate.

Wherein the difference point of light intensity is a point where the light intensity is different from the light intensity of the surrounding area.

Wherein the obtained position of the difference point of light intensity corresponding to the flexible substrate, and the position is treated as an abnormal position in the flexible substrate, which comprises: obtaining a first coordinate of the difference point of light intensity in a currently used coordinate system; converting the first coordinate into a coordinate system of the flexible substrate to obtain a second coordinate treated as an abnormal position where an abnormality exists in the flexible substrate.

Wherein when the position is treated as an abnormal position in the flexible substrate, which comprises: sending a photographing instruction to a photographing device including the information of the abnormal position to cause the photographing device to take an image of the abnormal position in the flexible substrate.

Wherein when the position is treated as an abnormal position in the flexible substrate, which further comprises: feeding back the information of the abnormal position to the display interface.

Wherein which further comprises: counting the number of the difference points of light intensity and feeding back the number of the difference points of light intensity to the display interface.

Wherein the flexible substrate comprises a transparent base substrate and a flexible material coated on the base substrate.

The present invention further provides a technical solution: providing a detection device for flexible substrate, wherein which comprises: a light source system for providing parallel light of equal intensity; a light intensity sensor is arranged in the light emitting direction of the light source system for detecting the light intensity distribution of the parallel light after transmitting through the flexible substrate; and a controller is connected to the light intensity sensor for obtaining the light intensity distribution by parallel light with the same intensity transmitted through the flexible substrate, obtaining a position of the difference point of light intensity corresponding to the flexible substrate and taking the position treated as an abnormal position in the flexible substrate.

Wherein the difference point of light intensity is a point where the light intensity is different from the light intensity of the surrounding area.

Wherein the controller is used to obtain a first coordinate of the difference point of light intensity in a currently used coordinate system, and convert the first coordinate into a coordinate system of the flexible substrate to obtain a second coordinate treated as an abnormal position where an abnormality exists in the flexible substrate.

Wherein which further comprises: a photographing system connected to the controller; the controller is further used to send a photographing instruction to the photographing system including information of the abnormal position; and the photographing system takes an image of the abnormal position in the flexible substrate.

Wherein the controller is further used to feed back the information of the abnormal position to the display interface.

Wherein the controller is further used to count the number of the difference points of light intensity and feedback the number of the difference points of light intensity to the display interface.

The present invention can be concluded with the following advantages, the detection method for flexible substrate of the present invention provided comprises: obtaining the light intensity distribution by parallel light with the same intensity transmitted through the flexible substrate; obtaining a position of the difference point of light intensity corresponding to the flexible substrate and taking the position treated as an abnormal position in the flexible substrate. Wherein the difference point of light intensity is a point where the light intensity is different from the light intensity of the surrounding area. When an abnormality occurs on the flexible substrate, because of the difference in light absorption coefficient between the abnormal position and the peripheral position, so there are difference points of light intensity after the light of the same intensity transmitted through the flexible substrate. By analyzing the intensity of light transmitted through the flexible substrate, the positions of difference point of light intensity are obtained from the light intensity distribution on the flexible substrate, so the abnormal positions can be obtained as the description of the present invention.

DESCRIPTION OF PREFERRED EMBODIMENT

Preferred embodiments of the present invention will be detailedly described herebelow. It should be noted that the variations of different embodiments should not be construed as the limitation of those embodiments of the present invention. To the contrary, by the detailed description of those embodiments, the present invention can be completely and thoroughly understood to the skilled in the arts. It should be noted that the dimensions, sizes of curtain portions, areas, layers have modified or exaggerated for better understanding. Numeral reference through different drawings represents the same element.

Organic materials (such as liquid PAA, PET, PEN, etc.) for manufacturing flexible substrates typically have a higher viscosity, so it is easy to occur an abnormality such as air bubbles or impurities in the manufacturing process of the flexible substrate. The existing detection technology is the detection of the surface of flexible substrate surface, which cannot detect whether there is any abnormal in the flexible substrate. If the flexible substrates with abnormalities enter the subsequent process of display, will result in the final preparation of the products appear poor display problems, and wasting manpower and material resources in the manufacturing process.

Figure 1:
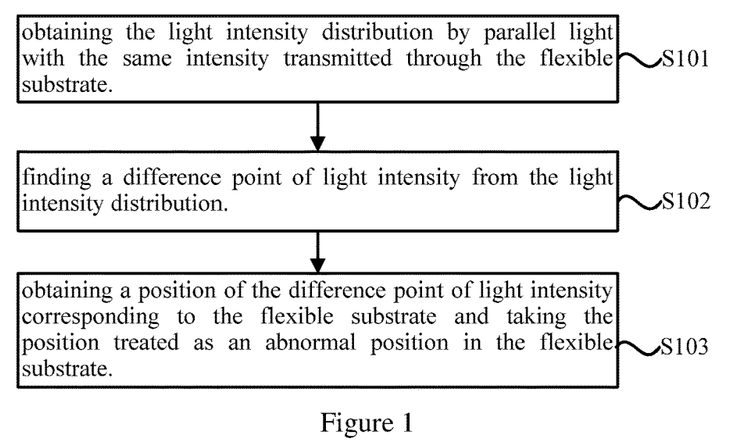
FIG. 1 is a flow chart of the first embodiment made in accordance to a detection method for flexible substrate of the present invention.

Referring to FIG. 1, FIG. 1 is a flow chart of the first embodiment made in accordance to a detection method for flexible substrate of the present invention. As shown in FIG. 1, the detection method of the present invention comprises:

S101, obtaining the light intensity distribution by parallel light with the same intensity transmitted through the flexible substrate.

In the present embodiment, the flexible substrate comprises a transparent base substrate and a flexible material coated on the base substrate, Since the flexible material coated on the base substrate generally has a high viscosity, abnormalities such as bubbles, impurities, or unevenness surface, are caused in the process of coating the flexible substrate on the base substrate. Wherein the base substrate may be a transparent glass substrate; the flexible material coated on the base substrate may be a liquid PAA, PET, PEN, and other organic materials.

When an abnormality occurs on a flexible substrate, absorption of light intensity at an abnormal position on the flexible substrate is different from absorption of light intensity at rest positions on the flexible substrate. Therefore, parallel light with the same intensity is used as the incident light to detect the flexible substrate, and the light intensity distribution is obtained after the parallel light with the same intensity transmitting through the flexible substrate. Specifically, one side of the flexible substrate faces the light source, and the other side faces light intensity sensors, and obtain the light intensity distribution by the light intensity sensors after the parallel light with the same intensity transmitting through the flexible substrate.

In the present embodiment, the light source for providing parallel light of the same intensity may be a surface light source, which provides parallel light with the same intensity directly. Or use a point light source and a backlight panel to compose a light source system, parallel light with the same intensity is emitted from the backlight panel by using the point light source to illuminate the backlight panel. It should be noticed that, the area of the parallel light provided is at least the same area of the flexible substrate regardless of the surface light source or the backlight panel is used to provide parallel light with the same intensity, so the entire flexible substrate is illuminated. In addition, sensing surface of the light intensity sensor should also be at least as the same area of the flexible substrate, so the light intensity sensor can obtain the intensity distribution of light transmitted through the flexible substrate completely.

S102, finding a difference point of light intensity from the light intensity distribution.

The light intensity distribution of light transmitted through the flexible substrate is obtained, and analyzing the light intensity distribution, so points which are different from the light intensity of the surrounding area can be obtained.

S103, obtaining a position of the difference point of light intensity corresponding to the flexible substrate and taking the position treated as an abnormal position in the flexible substrate.

The position of the difference point of light intensity corresponding to the flexible substrate can be obtained in accordance to the position of the difference point of light intensity obtained from the light intensity distribution in the step S102, and the position is an abnormal position where an abnormality occurs in the flexible substrate.

Figure 2:
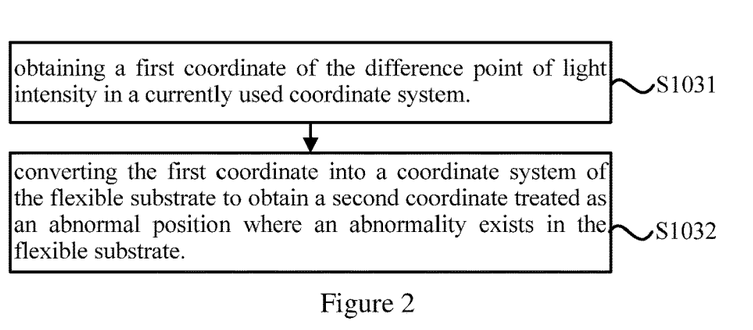
FIG. 2 is a flow chart of step S103 in FIG. 1.

Further, as shown in FIG. 2, the step S103 includes the steps of:

S1031, obtaining a first coordinate of the difference point of light intensity in a currently used coordinate system.

The first coordinate of the difference point of light intensity in the currently coordinate system can be obtained in accordance to the position of the difference point of light intensity obtained from the light intensity distribution in the step S102, In the present embodiment, because the obtained light intensity distribution is obtained by the light intensity sensor, so the currently coordinate system where the corresponding obtained difference point of light intensity in, is the coordinate system of the light intensity sensor. The first coordinate is the first coordinate of the difference point of light intensity in the coordinate system of the light intensity sensor.

S1032, converting the first coordinate into a coordinate system of the flexible substrate to obtain a second coordinate treated as an abnormal position where an abnormality exists in the flexible substrate.

The relative positional relationship between the flexible substrate and the light intensity sensor is set before the flexible substrate test, then the conversion relationship between the coordinate system of the flexible substrate and the coordinate system of the light intensity sensor is obtained. At this time, using the conversion relationship and the first coordinate of the difference point of light intensity in the coordinate system of the light intensity sensor in the S1031, the second coordinate of the difference point of light intensity in the coordinate system of flexible substrate can be obtained by calculating. This second coordinate is an abnormal position where an abnormality exists in the flexible substrate.

It should be noticed that, if there are bumps or pits appeared on surface of the flexible substrate, the thickness of the flexible substrate at the positions of the corresponding bumps or pits are different from the thickness of the flexible substrate of the rest area, absorption of light intensity at the position is also different from absorption of light intensity at rest positions, so difference points of light intensity also exist in the light intensity distribution obtained by the light intensity sensor. Therefore, the present embodiment can detect the abnormality not only in the flexible substrate but also on the surface of the flexible substrate.

In operation, the flexible substrate is placed between the light source and the light intensity sensor, wherein the light source is placed directly above or directly below the flexible substrate, and the light intensity sensor corresponding to the light source is placed directly below or directly above the flexible substrate, the positions of the light source, the light intensity sensor, and the flexible substrate are relatively fixed. Because a plurality of flexible substrates is required for detection in operation, therefore, the light source and the light intensity sensor are relatively fixed. Determining the placement where the flexible substrate placed in front of the light source and the intensity sensor, each time the flexible substrate is placed, the placement is the same.

Figure 3:
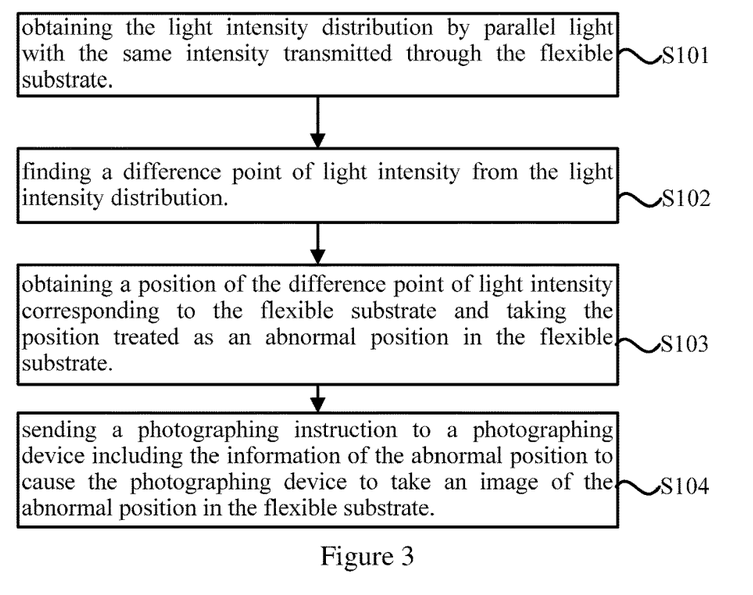
FIG. 3 is a flow chart of the second embodiment made in accordance to a detection method for flexible substrate of the present invention.

Referring the FIG. 3, FIG. 3 is a flow chart of the second embodiment made in accordance to a detection method for flexible substrate of the present invention. The present embodiment is obtained based on the improvement of the detection method for flexible substrate of the first embodiment shown in FIGS. 1 and 2, after the step S103 in the detection method for flexible substrate of the first embodiment, the present embodiment further comprises:

S104: sending a photographing instruction to a photographing device including the information of the abnormal position to cause the photographing device to take an image of the abnormal position in the flexible substrate.

When the abnormality is obtained in the flexible substrate after the step S103, in order to facilitate the skilled in the arts to directly observe specific situation of the abnormal position in the flexible substrate, sending a photographing instruction to a photographing device, the photographing instruction includes the information of the abnormal position in the flexible substrate. When the photographing device receives the photographing instruction, which includes the information of the abnormal position in the flexible substrate, the photographing device takes an image of the abnormal position in the flexible substrate based on the information of the abnormal position in the flexible substrate. Further, the image is stored after the photographing device has taken it.

It should be noticed that, the coordinate system of the photographing device needs to coincide with the coordinate system of the flexible substrate so as to take an image of the abnormal position on the flexible substrate.

Figure 4:
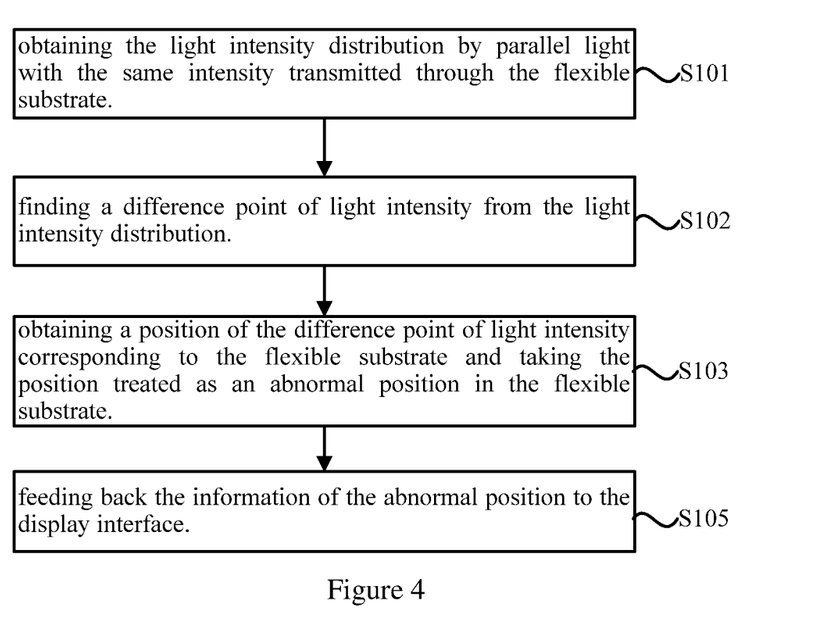
FIG. 4 is a flow chart of the third embodiment made in accordance to a detection method for flexible substrate of the present invention.

Referring to FIG. 4, FIG. 4 is a flow chart of the third embodiment made in accordance to a detection method for flexible substrate of the present invention. The present embodiment is obtained based on the improvement of the detection method for flexible substrate of the first embodiment shown in FIGS. 1 and 2, after the step S103 in the detection method for flexible substrate of the first embodiment, the present embodiment further comprises:

S105, feeding back the information of the abnormal position to the display interface.

When the abnormality is obtained in the flexible substrate after the step S103, in order to facilitate the skilled in the arts to directly obtain the information of the abnormal position in the flexible substrate, feeding back the information of the abnormal position to the display interface. Further, the information of the abnormal position fed back to the display interface is stored.

Figure 5:
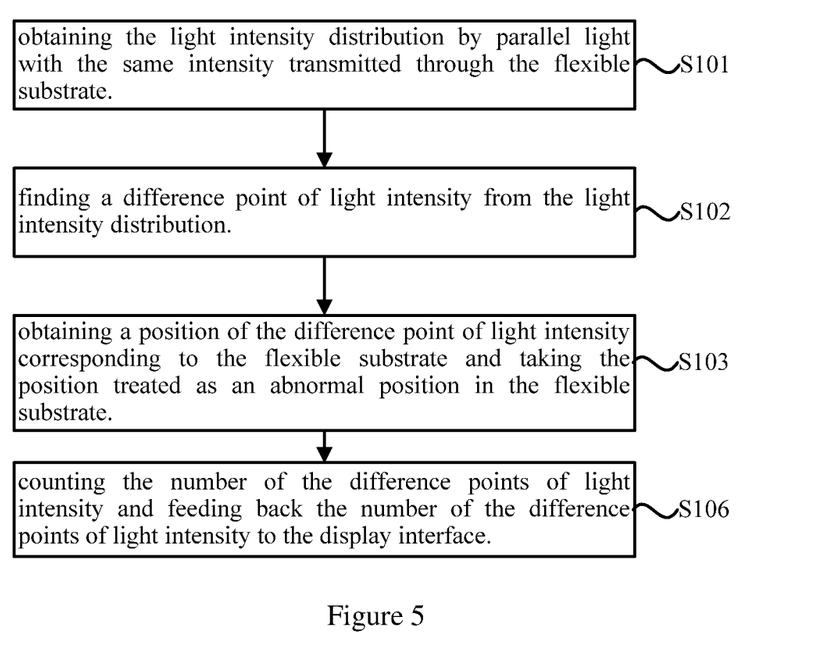
FIG. 5 is a flow chart of the forth embodiment made in accordance to a detection method for flexible substrate of the present invention.

Referring to FIG. 5, FIG. 5 is a flow chart of the forth embodiment made in accordance to a detection method for flexible substrate of the present invention. The present embodiment is obtained based on the improvement of the detection method for flexible substrate of the first embodiment shown in FIGS. 1 and 2, after the step S103 in the detection method for flexible substrate of the first embodiment, the present embodiment further comprises:

S106, counting the number of the difference points of light intensity and feeding back the number of the difference points of light intensity to the display interface.

When the abnormality is obtained in the flexible substrate after the step S103, in order to facilitate the skilled in the arts to directly analyze the abnormal position in the flexible substrate, counting the number of the difference points of light intensity and feeding back the number of the difference points of light intensity to the display interface. It is possible to directly determine whether the flexible substrate is directly eliminated or reworked based on the number of the difference points of light intensity obtained by the analysis.

It should be noticed that, the first embodiment, the second embodiment, the third embodiment, and the fourth embodiment of the flexible substrate detection method shown in FIGS. 1 to 5 may be combined with each other to form a new embodiment, and the specific content of the present embodiment is the same as the above-mentioned steps, therefore, no additional description is given herebelow.

Figure 6:
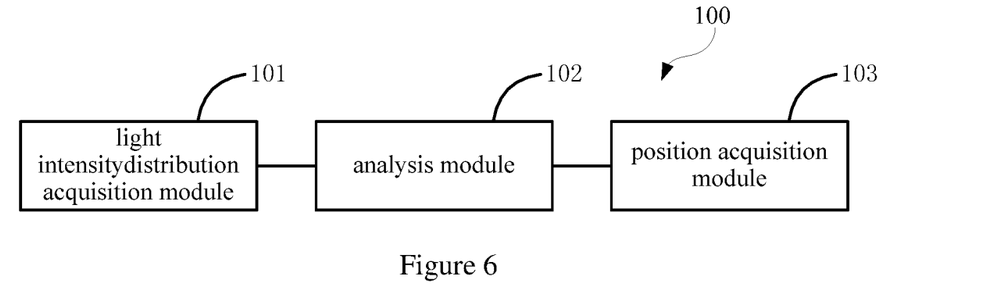
FIG. 6 is a functional block diagram of the first embodiment made in accordance to a detection system for flexible substrate of the present invention.

Referring to FIG. 6, FIG. 6 is a functional block diagram of the first embodiment made in accordance to a detection system for flexible substrate of the present invention. As shown in FIG. 6, the detection system 100 of the present embodiment comprises: a light intensity distribution acquisition module 101 for obtaining the light intensity distribution by parallel light with the same intensity transmitted through the flexible substrate; an analysis module 102 for finding a difference point of light intensity from the light intensity distribution, wherein the difference point of light intensity is a point where the light intensity is different from the light intensity of the surrounding area; and a position acquisition module 103 for obtaining a position of the difference point of light intensity corresponding to the flexible substrate, and the position is treated as an abnormal position in the flexible substrate.

Figure 7:
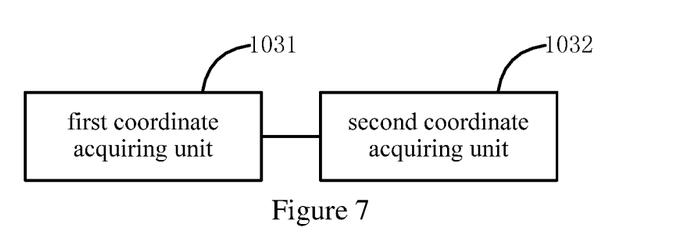
FIG. 7 is a functional block diagram of the position acquisition module in FIG. 6.

Further, as shown in FIG. 7, the position acquisition module 103 comprises: a first coordinate acquiring unit 1031 for obtaining a first coordinate of the difference point of light intensity in a currently used coordinate system; and a second coordinate acquiring unit 1032 for converting the first coordinate into a coordinate system of the flexible substrate to obtain a second coordinate treated as an abnormal position where an abnormality exists in the flexible substrate.

Figure 8:
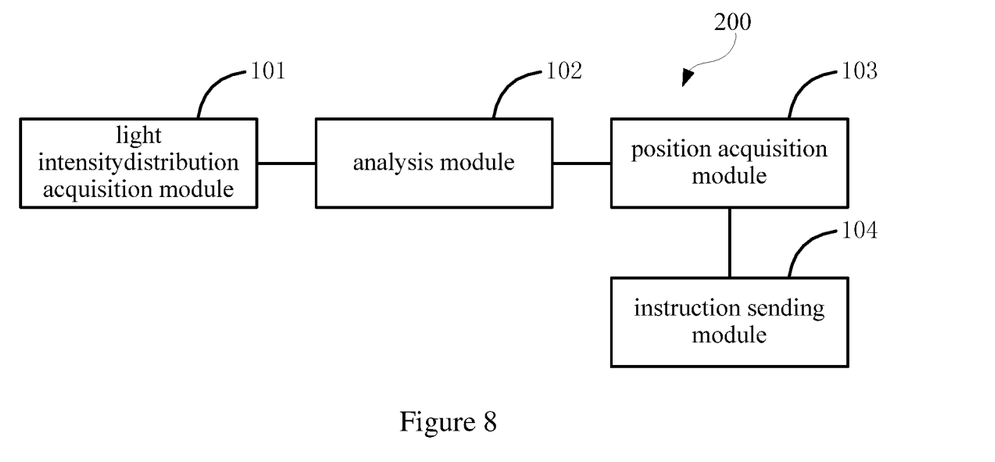
FIG. 8 is a functional block diagram of the second embodiment made in accordance to a detection system for flexible substrate of the present invention.

Referring to FIG. 8, FIG. 8 is a functional block diagram of the second embodiment made in accordance to a detection system for flexible substrate of the present invention. The detection system 200 of the present embodiment is obtained based on the improvement of the detection system 100 for flexible substrate of the first embodiment in FIG. 6, the following modules based on the detection system 100 are added: an instruction sending module 104 is used to send a photographing instruction to a photographing device including information of the abnormal position to cause the photographing device to take an image of the abnormal position in the flexible substrate.

Figure 9:
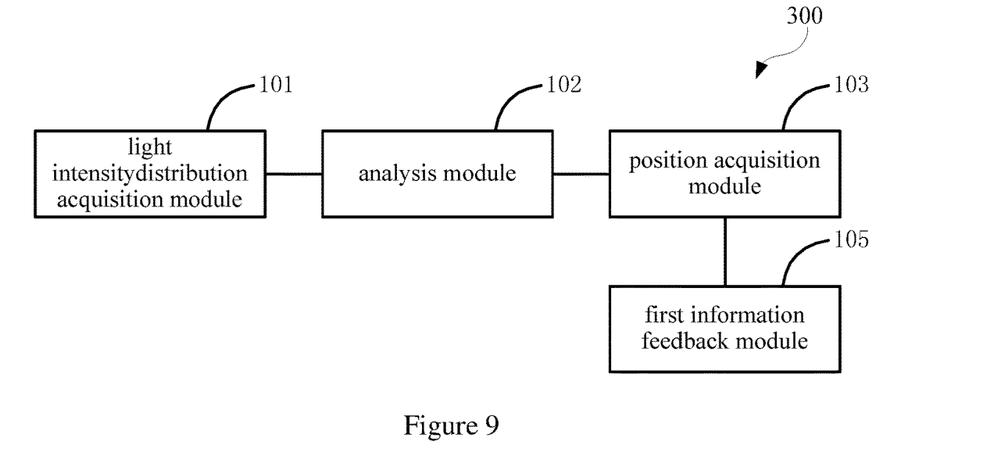
FIG. 9 is a functional block diagram of the third embodiment made in accordance to a detection system for flexible substrate of the present invention.

Referring to FIG. 9, FIG. 9 is a functional block diagram of the third embodiment made in accordance to a detection system for flexible substrate of the present invention. The detection system 300 of the present embodiment is obtained based on the improvement of the detection system 100 for flexible substrate of the first embodiment in FIG. 6, based on the detection system 100, the following modules are added: a first information feedback module 105 for feeding back the information of the abnormal position to the display interface.

Figure 10:
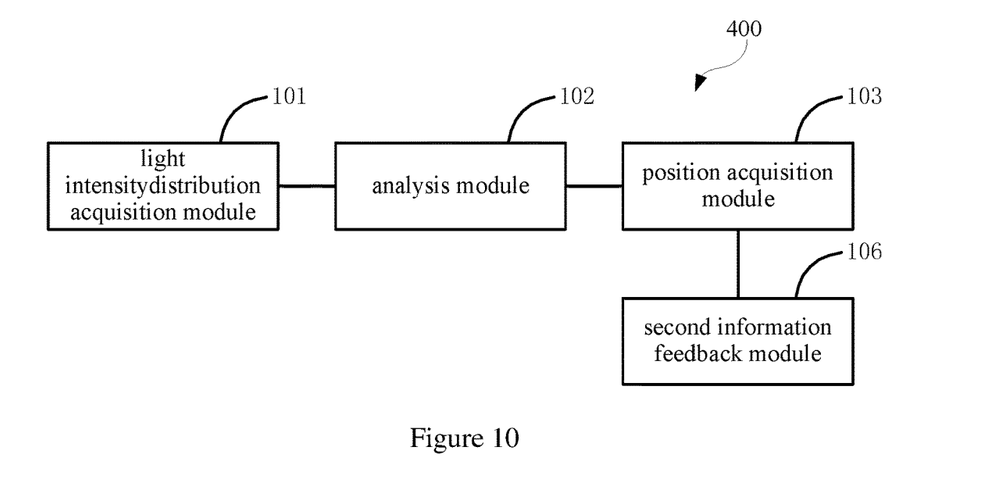
FIG. 10 is a functional block diagram of the forth embodiment made in accordance to a detection system for flexible substrate of the present invention.

Referring to FIG. 10, FIG. 10 is a functional block diagram of the forth embodiment made in accordance to a detection system for flexible substrate of the present invention. The detection system 400 of the present embodiment is obtained based on the improvement of the detection system 100 for flexible substrate of the first embodiment in FIG. 6, based on the detection system 100, the following modules are added: a second information feedback module 106 for counting the number of the difference points of light intensity and feeding back the number of the difference points of light intensity to the display interface.

The detection system 100, the detection system 200, the detection system 300, and the detection system 400 of the flexible substrate shown in FIGS. 6 to 10 are corresponding to the detection methods of the flexible substrate of the first embodiment, the second embodiment, the third embodiment, and the fourth embodiment shown in FIGS. 1 to 5, respectively. The specific execution of the modules is referred to the respective steps in the above-mentioned embodiments, therefore, no additional description is given herebelow.

It should be noticed that, the first embodiment, the second embodiment, the third embodiment, and the fourth embodiment of the flexible substrate detection method shown in FIGS. 6 to 10 may be combined with each other to form a new embodiment, and the specific content of the present embodiment is the same as the above-mentioned functional modules, therefore, no additional description is given herebelow.

Figure 11:
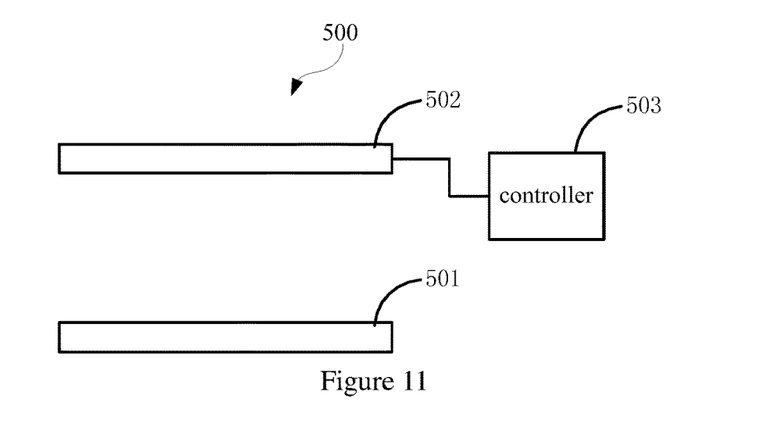
FIG. 11 is a structural illustration of the first embodiment made in accordance to a detection device for flexible substrate of the present invention.

Referring to FIG. 11, FIG. 11 is a structural illustration of the first embodiment made in accordance to a detection device for flexible substrate of the present invention. As shown in FIG. 11, the detection device 500 for flexible substrate of the present embodiment comprises: a light source system 501 for providing parallel light of equal intensity.

In the present embodiment, the light source system 501 may be a surface light source, which provides parallel light with the same intensity directly.

The light source system 501 further may be a light source system 501 composed by a point light source and a backlight panel, parallel light with the same intensity is emitted from the backlight panel by using the point light source to illuminate the backlight panel. It should be noticed that, the area of the parallel light provided is at least the same area of the flexible substrate regardless of the type of the light source system 501 is used to provide parallel light with the same intensity, so the entire flexible substrate is illuminated.

A light intensity sensor 502 is arranged in the light emitting direction of the light source system 501 for detecting the light intensity distribution of the parallel light after transmitting through the flexible substrate.

Sensing surface of the light intensity sensor 502 should also be at least as the same area of the flexible substrate, so the light intensity sensor 502 can obtain the intensity distribution of light transmitted through the flexible substrate completely.

A controller 503 is connected to the light intensity sensor 502 for obtaining the light intensity distribution by parallel light with the same intensity transmitted through the flexible substrate, obtaining a position of the difference point of light intensity corresponding to the flexible substrate and taking the position treated as an abnormal position in the flexible substrate. Wherein the difference point of light intensity is a point where the light intensity is different from the light intensity of the surrounding area.

In the present embodiment, the light source system 501 may be connected to the controller 503, the controller 503 controls the switch of the light source system 501; the light source system 501 may not be connected to the controller 503, and a switch independent of the controller 503 is arranged to the light source system 501.

Further, the controller 503 is used to feed back the information of the abnormal position to the display interface.

Further, the controller 503 is used to count the number of the difference points of light intensity and feedback the number of the difference points of light intensity to the display interface.

Figure 12:
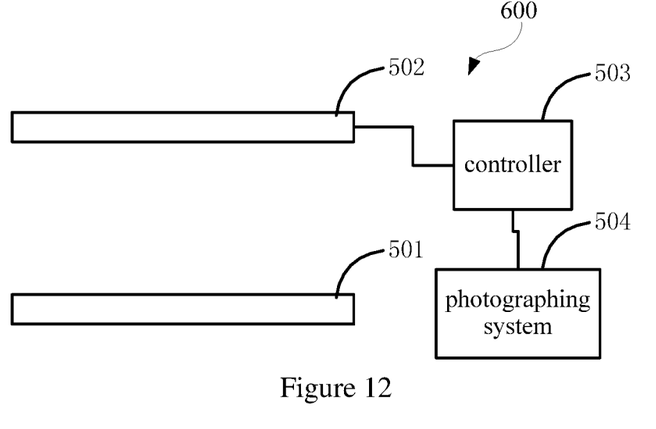
FIG. 12 is a structural illustration of the first embodiment made in accordance to a detection device for flexible substrate of the present invention.

Referring to FIG. 12, FIG. 12 is a structural illustration of the first embodiment made in accordance to a detection device for flexible substrate of the present invention. A photographing system 504 is added in the detecting device 600 of the present embodiment based on the detection device 500 shown in FIG. 11

The photographing system 504 is connected to the controller 503, and the controller 503 is further used to send a photographing instruction to a photographing system 504 including the information of an abnormal position, when the position is treated as an abnormal position in the flexible substrate.

The photographing system 504 is used to take an image of the abnormal position in the flexible substrate based on the photographing instruction.

It should be noticed that, the coordinate system of the photographing system 504 needs to coincide with the coordinate system of the flexible substrate so as to take an image of the abnormal position on the flexible substrate.

Embodiments of the present invention have been described, but not intending to impose any unduly constraint to the appended claims. Any modification of equivalent structure or equivalent process made according to the disclosure and drawings of the present invention, or any application thereof, directly or indirectly, to other related fields of technique, is considered encompassed in the scope of protection defined by the claims of the present invention.

The invention claimed is:

1. A detection system for flexible substrate, wherein which comprises:
    a light intensity distribution acquisition module for using a light intensity sensor to obtain the light intensity distribution by parallel light with the same intensity transmitted through the flexible substrate, wherein, the area of the parallel light is equal to the area of the flexible substrate, so the entire flexible substrate is illuminated; and a sensing surface of the light intensity sensor is at least as the same area of the flexible substrate;
    an analysis module for finding a difference point of light intensity from the light intensity distribution; and
    a position acquisition module for obtaining a position of the difference point of light intensity corresponding to the flexible substrate, and the position treated as an abnormal position in the flexible substrate;
    wherein the difference point of light intensity is a point where the light intensity is different from the light intensity of the surrounding area;
    wherein the position acquisition module comprises:
    a first coordinate acquiring unit for obtaining a first coordinate of the difference point of light intensity in a currently used coordinate system;
    a second coordinate acquiring unit for converting the first coordinate into a coordinate system of the flexible substrate to obtain a second coordinate treated as an abnormal position where an abnormality exists in the flexible substrate;
    wherein the detection system further comprises:
    an instruction sending module for sending a photographing instruction to a photographing device including information of the abnormal position to cause the photographing device to take an image of the abnormal position in the flexible substrate.

2. The detection system as recited in claim 1, wherein which further comprises:
    a first information feedback module for feeding back the information of the abnormal position to the display interface.

3. The detection system as recited in claim 1, wherein which further comprises:
    a second information feedback module for counting the number of the difference points of light intensity and feeding back the number of the difference points of light intensity to the display interface.

4. A detection method for flexible substrate, wherein which comprises:
    using a light intensity sensor to obtain the light intensity distribution by parallel light with the same intensity transmitted through the flexible substrate, wherein, the area of the parallel light is equal to the area of the flexible substrate, so the entire flexible substrate is illuminated; and a sensing surface of the light intensity sensor is at least as the same area of the flexible substrate;
    finding a difference point of light intensity from the light intensity distribution; and
    obtaining a position of the difference point of light intensity corresponding to the flexible substrate and taking the position treated as an abnormal position in the flexible substrate;
    wherein the difference point of light intensity is a point where the light intensity is different from the light intensity of the surrounding area.

5. The detection method as recited in claim 4, wherein the obtained position of the difference point of light intensity corresponding to the flexible substrate, and the position treated as an abnormal position in the flexible substrate, which comprises:
    obtaining a first coordinate of the difference point of light intensity in a currently used coordinate system; and
    converting the first coordinate into a coordinate system of the flexible substrate to obtain a second coordinate treated as an abnormal position where an abnormality exists in the flexible substrate.

6. The detection method as recited in claim 4, wherein when the position is treated as an abnormal position in the flexible substrate, which comprises:
    sending a photographing instruction to a photographing device including the information of the abnormal position to cause the photographing device to take an image of the abnormal position in the flexible substrate.

7. The detection method as recited in claim 4, wherein when the position is treated as an abnormal position in the flexible substrate, which comprising:

feeding back the information of the abnormal position to the display interface.

8. The detection method as recited in claim 4, wherein which further comprises:

counting the number of the difference points of light intensity and feeding back the number of the difference points of light intensity to the display interface.

9. The detection method as recited in claim 4, wherein the flexible substrate comprises a transparent base substrate and a flexible material coated on the base substrate.

10. A detection device for flexible substrate, wherein which comprises:

a light source system for providing parallel light of equal intensity;

a light intensity sensor arranged in the light emitting direction of the light source system for detecting the light intensity distribution of the parallel light after transmitting through the flexible substrate, wherein, the area of the parallel light is equal to the area of the flexible substrate, so the entire flexible substrate is illuminated; and a sensing surface of the light intensity sensor is at least as the same area of the flexible substrate; and     a controller connected to the light intensity sensor for obtaining the light intensity distribution by parallel light with the same intensity transmitted through the flexible substrate, and obtaining a position of the difference point of light intensity corresponding to the flexible substrate and taking the position treated as an abnormal position in the flexible substrate;

wherein the difference point of light intensity is a point where the light intensity is different from the light intensity of the surrounding area.

11. The detection method as recited in claim 10, wherein the controller is used to obtain a first coordinate of the difference point of light intensity in a currently used coordinate system, and convert the first coordinate into a coordinate system of the flexible substrate to obtain a second coordinate treated as an abnormal position where an abnormality exists in the flexible substrate.

12. The detection method as recited in claim 10, wherein which further comprises a photographing system connected to the controller;

and wherein the controller is further used to send a photographing instruction to the photographing system including information of the abnormal position;

the photographing system taking an image of the abnormal position in the flexible substrate.

13. The detection method as recited in claim 10, wherein the controller is further used to feed back the information of the abnormal position to the display interface.

14. The detection method as recited in claim 10, wherein the controller is further used to count the number of the difference points of light intensity and feedback the number of the difference points of light intensity to the display interface.

\* \* \* \* \*